(12) United States Patent
Jenkins

(10) Patent No.: US 7,115,399 B2
(45) Date of Patent: Oct. 3, 2006

(54) PINNA REFLEX ASSAY

(75) Inventor: Jennifer A. Jenkins, Rancho Santa Margarita, CA (US)

(73) Assignee: Allergan, Inc., Irvine, CA (US)

( * ) Notice: Subject to any disclaimer, the term of this patent is extended or adjusted under 35 U.S.C. 154(b) by 444 days.

(21) Appl. No.: 10/197,009

(22) Filed: Jul. 16, 2002

(65) Prior Publication Data

US 2003/0032891 A1 Feb. 13, 2003

(51) Int. Cl.
*C12P 19/26* (2006.01)

(52) U.S. Cl. .................. 435/84; 834/4; 73/861

(58) Field of Classification Search ............ 514/14, 514/312, 183; 119/417, 103; 600/546; 800/18; 424/236.1, 93; 435/84, 4; 73/861
See application file for complete search history.

(56) References Cited

U.S. PATENT DOCUMENTS

| | | | | |
|---|---|---|---|---|
| 4,065,561 | A * | 12/1977 | Gassel | 514/343 |
| 4,407,232 | A * | 10/1983 | Konz | 119/722 |
| 4,607,040 | A * | 8/1986 | Pearce et al. | 514/312 |
| 5,053,005 | A | 10/1991 | Borodic | |
| 5,435,999 | A * | 7/1995 | Austin | 424/93.1 |
| 5,562,907 | A * | 10/1996 | Arnon | 424/236.1 |
| 5,814,488 | A * | 9/1998 | Zhao et al. | 435/84 |
| 6,087,327 | A * | 7/2000 | Pearce et al. | 514/2 |
| 6,316,434 | B1 * | 11/2001 | Robichaud et al. | 514/183 |
| 6,358,926 | B1 * | 3/2002 | Donovan | 514/14 |
| 6,461,617 | B1 * | 10/2002 | Shone et al. | 424/236.1 |
| 6,500,436 | B1 * | 12/2002 | Donovan | 424/239.1 |
| 6,514,685 | B1 * | 2/2003 | Moro | 435/4 |
| 6,545,126 | B1 * | 4/2003 | Johnson et al. | 530/350 |
| 6,597,944 | B1 * | 7/2003 | Hadas | 600/546 |
| 6,632,977 | B1 * | 10/2003 | Kieffer et al. | 800/18 |

OTHER PUBLICATIONS

Adenis, J. P., et al., *Traitement des spasms faciaux par la toxine botulique A.*, J Fr Ophthalmol 1990;13(5) pp. 259-264.

Angaut-Petit, D., et al., *The levator auris longus muscle of the mouse: a convenient preparation for studies of short-and long-term presynaptic effects of drugs or toxins*, Neuroscience Letters 82(1987) 83-88.

Blitzer, A., et al., *Electromyographic findings in focal laryngeal dystonia (spastic dysphonia)*, Ann Otol Rhinol Laryngol 94:1985 pp. 591-594.

Brin, M.F, et al., *Localized injections of botulinum toxin for treatment of focal dystonia and hemifacial spasm*, Advances in Neurology, vol. 50, Dystonia 2, NY Raven Press 1988 pp. 599-608.

Casella, J.V., et al., *Habituation, prepulse inhibition, fear conditioning, and drug modulatonof the acoustically elicited pinna reflex in rats*, Bahavioral Neuroscience, 1986, vol. 100, No. 1, 39-44.

Caser, M., et al., *Startle repsonses measured in muscles innervated by facial and trigeminal nerves show common modulation*, Behavioral Neuroscience, 1989, vol. 103, No. 5, pp. 1075-1081.

Cohen, L., et al., *Treatment of focal dystonias of the hand with botulinum toxin injection*, Neurology Mar 1987 37(Suppl 1): 123-4.

(Continued)

*Primary Examiner*—Jewel Thompson
(74) *Attorney, Agent, or Firm*—Stephen Donovan; Martin A. Voet; Robert J. Barran

(57) ABSTRACT

Method for measuring potency of a substance, the method including; administering the substance to a mammal; subjecting the mammal to a stimulus; and monitoring a pinna reflex response of the mammal.

41 Claims, 4 Drawing Sheets

OTHER PUBLICATIONS

Elston, J.S., et al., *Paralytic strabismus: the role of botulinum toxin*, Br J. Ophthalmol Dec. 1985; 69(12):891-6.

Hambleton, R., *Clostridium botulinum toxins: a general review of involvement in disease, structure, mode of action and preparation for clinical use*, J. Neurol 1992 239:16-20.

Hatheway, C.L., Simpson, L.L., Ed., Academic Press Inc., 1989, Botulinum Neurotoxin and tetanus toxin, Chp. 1, *Bacterial Sources of clostridial neurotoxins*, pp. 3-24.

Jankovic, J., et al., *Therapeutic uses of botulinum toxin,*, N. Engl J Med Apr. 1991;324(17):1186-1194.

Jankovic, J., et al., *Botulinum A toxin for cranial-cervical dystonia*, Neurology 1987;37(4):616-23.

Juzans, P., et al., *Nerve Terminal sprouting in botulinum type-A treated mouse levator auris longus muscle*, Neuromusc. Disord, vol. 6, No. 3, pp. 177-185, 1996.

Pearce, L.B., et al., *Measurement of botulinum toxin activity: evaluation of the lethality assay*, Toxicology and applied Pharmacology 128,69-77 (1994).

Pilz, P.K., et al., *Comparative Threshold Studies of the Acoustic Pinna, Jaw and Startle Reflex in the Rat*, Physiology & Behavior, 1988, vol. 43, pp. 44-415.

Schantz, E. J., et al., *Microbiological Methods Standardized assay for clostridium botulinum toxins*, J. Assoc Off Anal Chem, 1978;61(1):96-9.

Schantz, E.J., et al., *Properties and use of botulinum toxin and other microbial neurotoxins in medicine*, Microbiol Rev Mar. 1992; 56(1):80-99.

Sesardic, D., et al., *Refinement and validation of an alternative bioassy for potency testing of therapeutic botulinum type A toxin*, Pharmacology & Toxicology 1996, 78(5) 283-288.

* cited by examiner

PINNA REFLEX ASSAY

BACKGROUND OF THE INVENTION

The present invention relates to an assay method, for example, using the pinna reflex, and is more particularly directed to an assay method for determining the potency of a substance, for example, botulinum toxin type A.

Botulinum toxin, for example, botulinum toxin type A, has been used in the treatment of a number of neuromuscular disorders and conditions involving muscular spasm, such as strabismus, blepharospasm, spasmodic torticollis (cervical dystonia), oromandibular dystonia, spasmodic dysphonia (laryngeal dystonia) and the like. The toxin binds rapidly and strongly to presynaptic cholinergic nerve terminals and inhibits the exocytosis of acetylcholine. This results in local paralysis thereby relaxing the muscle afflicted by spasm.

For one example of treating neuromuscular disorders, see U.S. Pat. No. 5,053,005, which suggests treating curvature of the juvenile spine, i.e., scoliosis, with an acetylcholine release inhibitor, preferably botulinum toxin A. For the treatment of strabismus with botulinum toxin type A, see Elston, J. S., et al., British Journal of Ophthalmology, 1985, 69, 718–724 and 891–896. For the treatment of blepharospasm with botulinum toxin type A, see Adenis, J. P., et al., J. Fr. Ophthalmol., 1990, 13 (5) at pages 259–264. For treating spasmodic and oromandibular dystonia torticollis, see Jankovic et al., Neurology, 1987, 37, 616–623. Spasmodic dysphonia has also been treated with botulinum toxin type A. See Blitzer et al., Ann. Otol. Rhino. Laryngol, 1985, 94, 591–594. Lingual dystonia was treated with botulinum toxin type A according to Brin et al., Adv. Neurol. (1987) 50, 599–608. Cohen et al., Neurology (1987) 37 (Suppl. 1), 123–4, discloses the treatment of writer's cramp with botulinum toxin type A.

Botulinum toxin is a generic term embracing the family of toxins produced by the anaerobic bacterium *Clostridium botulinum*. To date seven immunologically distinct neurotoxins serotype have been identified. These have been given the designations A, B, $C_1$, D, E, F and G. For further information concerning the properties of the various botulinum toxins see, Jankovic and Brin, *The New England Journal of Medicine*, Vol. 324, No. 17, 1990, pp. 1186–1194, and see, the review by Charles L. Hatheway in Chapter 1 of the book entitled *Botulinum Neurotoxin and Tetanus Toxin*, L. L. Simpson, Ed., published by Academic Press Inc. of San Diego, Calif., 1989.

Botulinum toxin is obtained commercially by growing cultures of *C. botulinum* in a fermenter and then harvesting and purifying the fermented mixture in accordance with known techniques. Botulinum toxin type A, the toxin type generally utilized in treating neuromuscular conditions, is currently available commercially from several sources including from Allergan, Inc., Irvine, Calif., under the trade name BOTOX7, and from Porton Products Ltd. UK, under the trade name DYSPORT7.

The active component of the botulinum toxin type A in therapeutic preparations is complexed to the non-toxic component haemagglutinin, and is present in extremely small amounts. The specific activities of different formulations vary because retention of biological potency during the formulation freeze-drying process is not reproducible. This results in different ratios of active to inactive toxin and makes it impossible to express the unit activity of this compound in terms of mass (Hambleton, *J Neurol* 1992, 239:16–20; Schantz and Johnson, *Microbiol Rev* 1992, 56:80–99).

At present the biological potency of therapeutic preparations of type A botulinum toxin is expressed in terms of mouse $LD_{50}$ units. Contrary to general belief, the mouse unit is not a standardized unit. It is well documented that the assay to determine the potency of botulinum toxin type A in mouse $LD_{50}$ units is prone to significant inter-laboratory variability (Schantz and Kautter, *J Ass of Anal Chem* 1978, 61:96–99). One study designed to standardize a Botulinum type A toxin assay involved 11 different laboratories (Sesardic et al, *Pharacol Toxico* 1996, 78:283–288). In this study there was found to be up to a 10-fold difference in results. This variability in mouse $LD_{50}$ is not unique to assays involving botulinum toxin. In fact, because of the variability of this assay, a number of regulatory agencies have abandoned requiring the routine use of $LD_{50}$ for toxicity testing for a number of chemicals, solvents, cosmetics and drugs (Pearce et al, *Toxicol App Pharm* 1994, 128:69–77).

The expanding medical importance of botulinum toxins has increased the need for, and placed a premium on, the precise analysis of biological activity contained in preparations of botulinum toxin type A for both clinical use and laboratory investigation.

It would be advantageous to provide a more precise measurement of toxin activity based on a non-lethal exposure of botulinum toxin type A to rats.

The pinna reflex is a part of the overall acoustic startle response that occurs in certain mammals, including the rat. The characteristic feature of the acoustic startle response in mammals is a pattern of generalized muscular contractions with short latencies. Reflex action starts in the face and neck and spreads down the body, producing a transitory crouch-like gesture. The prominent motor component of the startle response is a flexor contraction.

Response probability and magnitude of the reflex rises with an increase in stimulus intensity. In addition to the response of the body muscles, the whole body startle, several muscles of the head are also involved in the startle reaction. Additionally, a flexion of the pinna occurs in some mammals including rats. This is called the Preyer reflex. Pinna motor reactions caused by intense acoustic stimulation are described as an essential component of the startle reaction with response similar to the whole-body startle. However, this movement of the ears may be a separate reflex.

SUMMARY OF THE INVENTION

New methods for measuring the potency of a substance have been discovered. In many instances, the present methods provide substantial benefits, for example, in terms of increased precision and reproducibility of results, relative to prior potency measuring methods. Moreover, the present methods are relatively straightforward, easy to practice and provide cost effective potency determinations. "Potency" as used herein refers to an effect, for example, denervating effect, per quantity of substance administered to a mammal. In one embodiment, the potency is defined by an $ED_{50}$. An $ED_{50}$, for example, is an effective dose to reduce the pinna reflex response of a rat by 50%. The quantity of the substance may be, for example, a mass quantity of solid or a volumetric quantity of liquid. A Asubstance@ as used herein refers to any matter of a particular or definite chemical constitution. For example, a substance may be a chemical compound, a mixture of chemical compounds, a composition and the like. A substance may be a toxin, for example, a bacterial toxin, such as a Clostridial toxin.

In a broad aspect of this invention, methods for measuring potency of a substance are provided. Such methods comprise administering the substance to a mammal; subjecting the mammal to a stimulus; and monitoring a pinna reflex response of the mammal to the stimulus.

In the present methods, a substance is administered to a mammal. Any suitable type of administration may be employed, provided that the administration is such that at some non-lethal dose of the substance the mammal, that has been administered the substance, exhibits a pinna reflex response to the stimulus. Administration may be by application to a surface of a muscle; may be orally; may be applied directly to the skin of the mammal; and the like administration techniques. The administration may be by injection, for example, intravenous injection, intramuscular injection, subcutaneous injection, and the like. In one particularly useful embodiment, the administration of the substance is by injection into a levator auris longus muscle of the mammal.

The substance may be administered in one or more dose levels to one or more mammals of the same species and strain.

In one embodiment, the substance is a botulinum toxin, such as serotype A, serotype B, serotype $C_1$, serotype D, serotype E, serotype F and mixtures thereof. Botulinum toxin type A is a substance the potency of which is very effectively determined in accordance with the present invention.

The substance may also include a mixture of components. For example, the substance may include one or more botulinum toxin serotypes that may be mixed together. The substance may also include a combination of components. For example, one or more botulinum toxin serotypes may be administered separately, in a sequential order.

The mammal may be, for example, a mouse a guinea pig, a rabbit or a rat. In preferred embodiment, the mammal is a rat.

Prior to, or after, administration of the substance, the mammal may be, and preferably is, placed in a confined space. The mammal may be, and preferably is, placed in a restraint prior to or after the administration. More preferably, the mammal is placed in a confined space and placed in the restraint prior to or after substance administration. Any suitable restraint may be employed, provided that the restraint allows, and preferably facilitates, monitoring a pinna reflex response of the mammal in the restraint. The restraint may comprise an apparatus that holds or anchors the head of the mammal, for example, a rat, in a fixed position.

The mammal is subjected to a stimulus, for example, after substance administration. The stimulus may have an effect on the sense of the mammal. "Sense" as used herein refers to a mechanism of the mammal involving a sensory organ that is effective to provide a pinna reflex response to a stimulus. In one embodiment the stimulus is an acoustic stimulus. The acoustic stimulus dB SPL may be set at any level that will cause an effect on the mammal. In another embodiment the stimulus is a visual stimulus. Subjection of the mammal to the stimulus may be repeated at set time intervals.

The pinna reflex response may comprise a flexion of the ear or ears of the mammal.

The pinna reflex response of the mammal to the stimulus is monitored. The monitoring may include recording of the pinna reflex response invoked by the stimulus. The monitoring of the response may be repeated at time intervals or may be continuous over a period of time. In one embodiment, the time intervals are predetermined. Any suitable monitoring of the pinna reflex response of the mammal may be employed provided it is effective to differentiate the response based on the amount or dose of substance administered and preferably based on the time interval from administration of the substance. In one particularly useful embodiment, the monitoring includes use of a photocell device. The monitoring may, and preferably does, include measuring the flexion of an ear of the mammal.

The measuring of the flexion of an ear of the mammal may include use of a photocell device. For example, the photocell device may be positioned in front of the ear or ears of the mammal.

In a particularly useful embodiment, the pinna reflex response is correlated to the potency of the substance.

The present methods may include measuring either the latency or magnitude of the pinna reflex response. In one embodiment, both the latency and magnitude of the response are measured. "Magnitude" as used herein refers to the size of the pinna reflex response. Magnitude may be measured by the time of the response after the mammal is subjected to the stimulus. For example, if the response being monitored is the movement of an ear, the magnitude of that response is correlated to the time that the ear of the mammal is moved from its resting position after the mammal is subjected to the stimulus. "Latency" as used herein refers to the amount of time that lapses between subjecting a mammal to a stimulus and the start of the pinna reflex response.

In one embodiment, an activity of a muscle is monitored. The monitoring of the muscle activity may be accomplished using any suitable technique and/or equipment effective to perform this function effective to differentiate the muscle activity based on the amount of substance administered and or the time from substance administration. Advantageously, such muscle activity monitoring includes use of an electromyograph. The monitoring of an activity of the muscle may be done by appropriately positioning an electromyographical probe. The monitoring of the activity of the muscle may be repeated at time intervals or may be continuous over a period of time. In one embodiment, the time intervals are predetermined.

The monitoring of muscle activity preferentially includes recording of muscle activity. For example, information provided by the instrumentation used, such as an electromyographical probe, relating to the activity of a muscle may be recorded.

In one embodiment, the muscle activity is related or correlated to the potency of the substance, for example, using information on substance latency provided by an electromyographical probe. Potency is related or correlated to the amplitude of the muscle activity, for example, using information on amplitude provided by the electromyographical probe. "Amplitude" as used herein refers to the size or intensity of a deviation in muscle activity resulting from the administration of the substance. In addition, potency is related or correlated to frequency of the muscle activity, for example, using information on frequency provided by the electromyographical probe. "Frequency" as used herein refers to a measure of the activity of the muscle per unit of time resulting from the administration of the substance. In one embodiment, potency is related or correlated to combinations of two or more of latency, amplitude and frequency.

Any and all features described herein and combinations of such features are included within the scope of the invention provided that such features of any such combination are not mutually exclusive.

These and other aspects and advantages of the present invention are apparent in the following detailed description and claims.

DETAILED DESCRIPTION OF THE INVENTION

Figure 1:
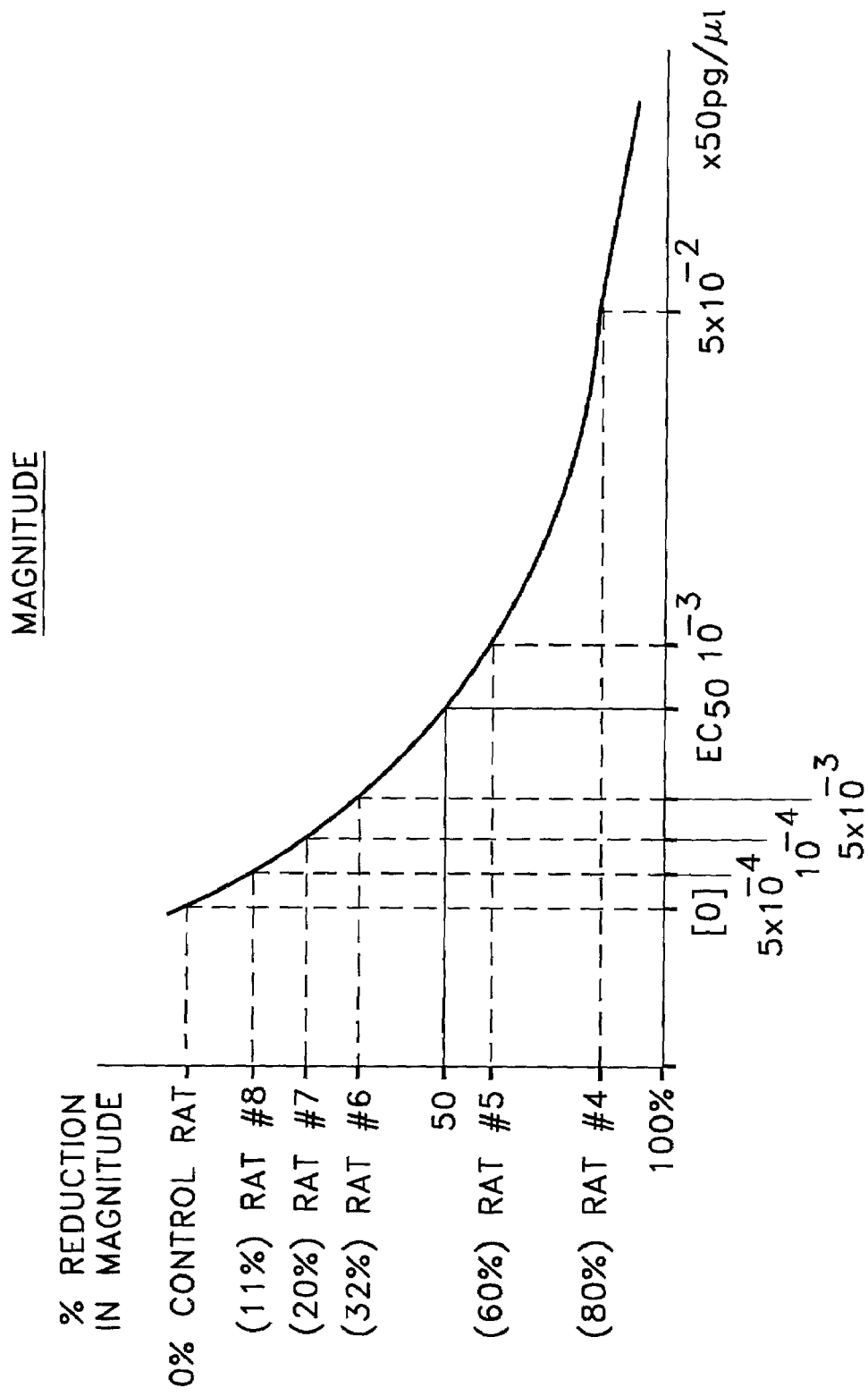
FIG. 1 is a dose response curve showing reduction in magnitude of pinna reflex response in rats as measured in accordance with the present invention.

The present invention relates to methods to accurately determine the potency of a substance. In one embodiment the substance is a drug. In a preferred embodiment the substance is a toxin, such as a bacterial toxin, for example, a Clostridial toxin. Even more preferably, the Clostridial toxin is a botulinum toxin, such as botulinum toxin type A. The present invention measures the potency of the substance based on changes in a measured pinna reflex response to an induced stimulus in a mammal.

Assay Apparatus and Setup

An assay apparatus for use in accordance with the present invention functions to measure a pinna reflex response of a mammal to a stimulus. This response to stimulus is affected by administering a substance, such as botulinum toxin type A, to the mammal.

The assay apparatus may include a head holder, photocell, light source and manipulator arm.

In one embodiment of the present invention, the head of a mammal, for example a rat, is restrained or secured in place with the aid of the head holder. One purpose of the head holder is to hold the pinna stable relative to the assay apparatus. In order to secure the rat's head to the head holder, the rat may be spinally transected under anesthesia in a standard stereotaxic instrument. For example, a 2–3 cm midline incision is made on the dorsal surface of the rat, centered over the second thoracic vertebra (T-2). The muscle overlying this and neighboring vertebrae is cut in order to expose the vertebral column. Rongeurs may be used to remove the T-2 vertebra, and expose the spinal cord. The spinal cord is then lifted and transected completely. The opening in the vertebral column is patched with a compound comprising a filling agent, for example Gelfoam, and may then be covered with a topical bacteriostatic dressing.

A bolt is attached to the skull of the mammal. In one embodiment, the head is positioned in a flat plane, and a 2 cm midline incision is made in the skin overlying the skull at the bregma. With the Fascia and skin retracted, four holes may be drilled concentrically around bregma where screws are attached to the skull. A cap screw is lowered, cap side down, onto the pedestal and cemented into place. Following a sufficient recovery period, approximately 24 hours, the cap screw is secured into place by attachment of the screw to a bracket comprising the head holder of the assay apparatus.

Movement of the pinna preferably is measured using a photocell device. The photocell device includes, for example, a phototransistor situated opposite a light source. In this example, both the light source and photocell are attached to a manipulator arm. The manipulator arm allows for the placement of the photocell device so that the pinna blocks the light source from the photocell. The mammal's ear may be only partially opaque and some light is allowed to pass though to the phototransistor. In this instance, in one embodiment, the photocell device will be positioned so that the voltage output of the photocell is set to a standard level, for example, 2.0 volts.

An acoustic stimulus may be used. In one embodiment, the acoustic stimulus may be made by an air blast. In another embodiment, the acoustic stimulus is produced by a solenoid that when activated, causes a pin within the solenoid to strike a solid surface in a reproducible way. Other examples of acoustic stimuli that may be used include dropping of clay or acrylic balls from various heights. Any source of acoustic vibration that reasonably can be used to elicit a startle response is covered within the scope of this invention. In addition, the acoustic stimulus dB SPL may be set at any level that will cause an effect on the mammal, that is a pinna reflex response.

In addition, pinpoint stimulus, as is known to those skilled in the art, may be used within the scope of the present invention.

When positioned for testing, the mammal's pinna interrupts the light beam of the photocell device. Flexion of the pinna allows light to activate the phototransistor producing a photocell output proportional to the amount of pinna movement. The photocell is attached to an oscilloscope, which produces a tracing of the photocell output in response to flexion of the pinna. The photocell output voltage is fed in parallel to the oscilloscope and a specially designed sample-and-hold circuit. This sample-and-hold circuit samples the peak voltage that occurs during a set period immediately following the onset of the stimulus. The set period may be, for example, 60 milliseconds. The output of the sample-and-hold circuit may be digitized then fed to a monitor and/or a printer. This allows for recording of latency, which may be a measure of the amount of time that lapses after the occurrence of the stimulus and before a response occurs.

In another embodiment of the invention, the pinna reflex response is recorded in terms of magnitude, which may be a measure of the amount of time the pinna are moved out of the path of the light beam in response to stimulus. In one embodiment, both latency and magnitude are recorded.

Flexion of a mammal's pinna in response to stimulus may be measured using an accelerometer which may comprise piezoelectric material. During the stimulus-invoking event, the mammal may be loosely restrained. For example, the mammal may be confined in a startle box as is familiar to those skilled in the art.

There are at least two types of piezoelectric material that may comprise the accelerometer in accordance with the present invention: 1) quartz and 2) polycrystalline ceramics. Both of these materials may operate by generating a surface charge when exposed to an external force, for example, acceleration.

In one embodiment, a piezo strip (piezo film) is attached to an ear of a mammal by, for example, an adhesive mount. In another embodiment, a piezo sensor is attached to the ear of a mammal by an adhesive or by an adhesive strip. Examples of substances that may be used as an adhesive in accordance with the present invention are petro wax, epoxies, dental cement, hot glues, instant glues, and duct putty.

In one embodiment, a piezo strip is attached to a pinna of a mammal by dental cement. The piezo strip is attached such that a pinna reflex in response to a stimulus imposes a force on the piezo strip. This force is proportional to the acceleration of the ear during flexion. The force applied to the piezo strip may result in a charge accumulating in the piezo strip that is proportional to the acceleration of the ear. Electrodes are attached to the piezo strip and collect the generated charge. Wires may be used to transmit the charge from the piezo strip to a recording and/or display device or to a signal conditioner. The signal conditioner may be used to condition the signal before it is input to a display and/or recording device.

In another embodiment, a piezo sensor is attached to the ear of a mammal by an adhesive strip such that a pinna reflex in response to a stimulus imposes a force on the piezo sensor. This force is proportional to the acceleration of the ear during flexion. The force applied to the piezo sensor may result in a charge accumulating in the piezo sensor that is proportional to the acceleration of the ear.

Electrodes are attached to the piezo sensor and collect the generated charge. Wires may be used to transmit the charge from the piezo sensor to a recording and/or display device or to a signal conditioner. The signal conditioner may be used to condition the signal before it is input to a display and/or recording device.

The assay apparatus may include an electromyograph (EMG) or equivalent device. In one embodiment, an electrode plug may be affixed to the scull of the rat with dental cement and then secured in place by two or more screws. One of the screws may be used as an indifferent electrode. Platinum wires may be used as EMG electrodes with at least one of these wires run from the electrode cap into the levator auris muscle. For example, a single strand of platinum wire insulated with Teflon7, except for approximately 5 mm from the tip of the wire, may be inserted into a 22-gauge hypodermic needle so that approximately 2 mm of the uninsulated wire extends from the tip of the needle. The tip of the wire may then be bent back over the bevel of the needle making a hook structure in the wire. After making small incisions in the skin the needle may be inserted into the levator auris longus muscle and the hook in the wire anchored into the muscle. The needle may be removed and the electrode sutured to the muscle.

Assay Procedure

The pinna reflex assay method of the present invention is based, in part, on measuring and recording a change in response to a stimulus in a mammal that has been administered a substance.

In one embodiment, a substance is injected into a rat in an amount sufficient to change the pinna reflex response to a stimulus, for example, an acoustic stimulus. The injection may be made intravenously. Preferably, the injection is made in the region of, or into, a nerve or muscle. For example, if the substance injected is botulinum toxin type A and the injection is made into the region of the levator auris longus muscle partial paralysis of the muscle is induced. In this embodiment, the response of the muscle to an acoustic stimulus may be altered. This alteration may be measured by, for example, measuring a change in appendage movement and/or by measuring a change in muscle activity.

In one embodiment, the change in contraction of the levator auris longus muscle in response to an acoustic stimulus is measured and recorded. When the levator auris longus muscle contracts, movement of the pinna results (pinna reflex response). The movement of the pinna in response to an acoustic stimulus may be measured using the apparatus described above. At least two parameters may be quantitated in order to measure the pinna reflex, for example, latency and magnitude. Latency is measured in terms of the delay in response to stimulus. This may be a delay in movement of the pinna in response to an acoustic stimulus. Magnitude is a quantitative representation of the movement of the pinna during response to a stimulus. For example, the magnitude may be related to the distance the pinna moves in response to a stimulus and/or the length of time the ear is moved from a resting position.

The change in activity in a muscle, for example, the levator auris longus, in response to a stimulus is measured and recorded. This measurement preferably involves latency, frequency and amplitude. Latency may be a measure of the time between onset of the acoustic stimulus and the peak of the ensuing action potential. Frequency may be a measure of the electrical activity of the muscle per unit of time. Amplitude may be a measure of the intensity, or size, of the action potential in response to the stimulus measured in, for example, microvolts. In a preferred embodiment electrical activity in a muscle is measured using an electromyograph (EMG).

In one embodiment, change in both pinna reflex and electrical activity in a muscle in response to a substance injection are measured and recorded.

The following non-limiting examples illustrate certain aspects of the present invention.

Examples 1–4 are methods to determine the potency of botulinum toxin type A.

Example 6 shows the reproducibility of potency determination for botulinum type A using the method of the present invention.

EXAMPLE 1

A batch of botulinum toxin type A is prepared by a standard methodology. A serial dilution of the toxin is done by a standard methodology. The stock solution of the toxin is set at an approximate concentration of 50 picograms of botulinum toxin type A/microliter. Five fold dilutions are done with the final serial dilution factors ranging from 1.0 (stock solution) to $1.0 \times 10^{-4}$. In addition, rats, one for each serial dilution, are prepared for a potency assay as described elsewhere herein. 1.0 microliter of each of the nine dilutions is injected into the levator auris longus muscle of one of the rats as follows:

Rat No. 1, dilution factor=1.0
Rat No. 2, dilution factor=$5.0 \times 10^{-1}$
Rat No. 3, dilution factor=$1.0 \times 10^{-1}$
Rat No. 4, dilution factor=$5.0 \times 10^{-2}$
Rat No. 5, dilution factor=$1.0 \times 10^{-2}$
Rat No. 6, dilution factor=$5.0 \times 10^{-3}$
Rat No. 7, dilution factor=$1.0 \times 10^{-3}$
Rat No. 8, dilution factor=$5.0 \times 10^{-4}$
Rat No. 9, dilution factor=$1.0 \times 10^{-4}$ A Control Rat is injected with 1.0 microliter of sterile saline. After a 24 hour incubation period Rat No. 1 is dead. Rat No. 2 is completely paralyzed. The remaining rats are examined using the pinna reflex assay described in the detailed description of the invention. Rat No. 3 is non-responsive to acoustic stimulation. Change in magnitude for the pinna reflex response is measured for Rats No. 4, 5, 6, 7, 8 and a Control Rat using the assay apparatus. For each of these rats, the magnitude is determined using seven independent measurements each taken at a 5 minute interval.

An average is taken of the seven measurements for each of the five rats tested. These mean values are plotted on a dose response curve in order to calculate a magnitude $ED_{50}$ value for the stock botulinum toxin type A solution (FIG. 1). It can be seen in FIG. 1 that the magnitude $ED_{50}$ value (potency) for the stock botulinum toxin solution is between $5 \times 10^{-3} \times (50\ picograms/microliter)$ and $10^{-3} \times (50\ picograms/microliter)$ per rat. That is, the magnitude of the pinna reflex response of a rat injected with between $5 \times 10^{-3} \times (50\ picograms/microliter)$ and $10^{-3} \times (50\ picograms/microliter)$ of botulinum toxin type A will be 50% that of the Control Rat, where the Control Rat has the largest measured magnitude and the Rat No. 4 has the lowest measured magnitude.

EXAMPLE 2

Rats are injected with botulinum toxin type A as in Example 1. Change in latency for the pinna reflex response is measured for Rats No. 4, 5, 6, 7, 8 and the Control Rat using the assay apparatus. For each of these rats, the latency is determined using seven independent measurements each taken at a 5 minute interval.

Figure 2:
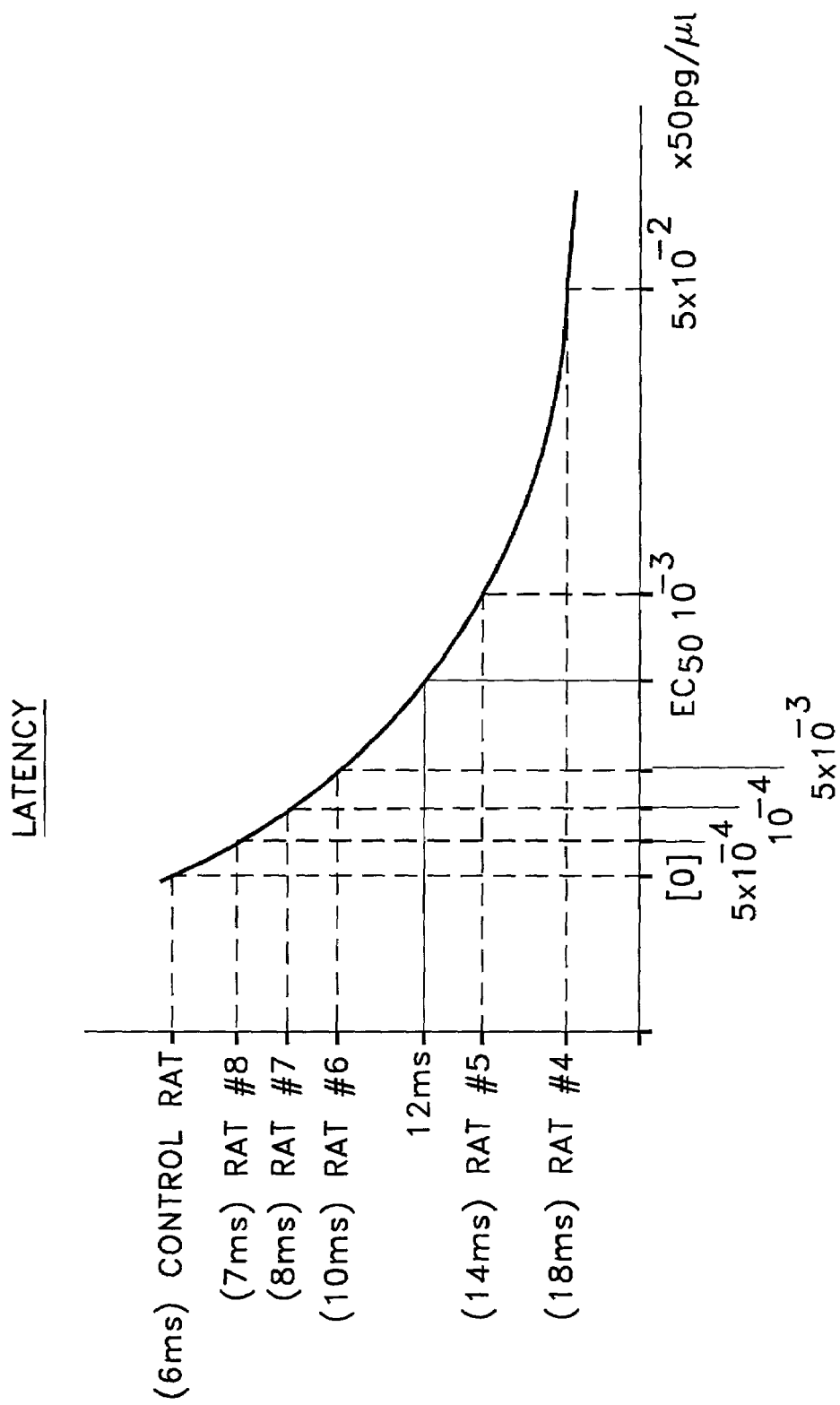
FIG. 2 is a dose response curve showing change in pinna reflex response latency in rats as measured in accordance with the present invention.

An average is taken of the seven measurements for each of the five rats tested. These mean values are plotted on a dose response curve in order to calculate a latency $ED_{50}$ value for the stock botulinum toxin type A solution (FIG. 2). It can be seen in FIG. 2 that the latency $ED_{50}$ value (potency) for the stock botulinum toxin solution is between $5 \times 10^{-3} \times (50\ picograms/microliter)$ and $10^{-3} \times (50\ picograms/microliter)$ per rat. That is, the latency of the pinna reflex response of a rat injected with between $5 \times 10^{-3} \times (50\ picograms/microliter)$ and $10^{-3} \times (50\ picograms/microliter)$ per rat of botulinum toxin type A is half way between the Control Rat and Rat No. 4, where the Control Rat has the shortest measured latency and Rat No. 4 has the longest measured latency.

EXAMPLE 3

Rats are injected with botulinum toxin type A as in Example 1. Change in amplitude for the EMG measurement is measured for Rats No. 4, 5, 6, 7, 8 and the Control Rat using the assay apparatus previously described. For each of these rats, the amplitude is determined using seven independent measurements each taken at a 5 minute interval.

Figure 3:
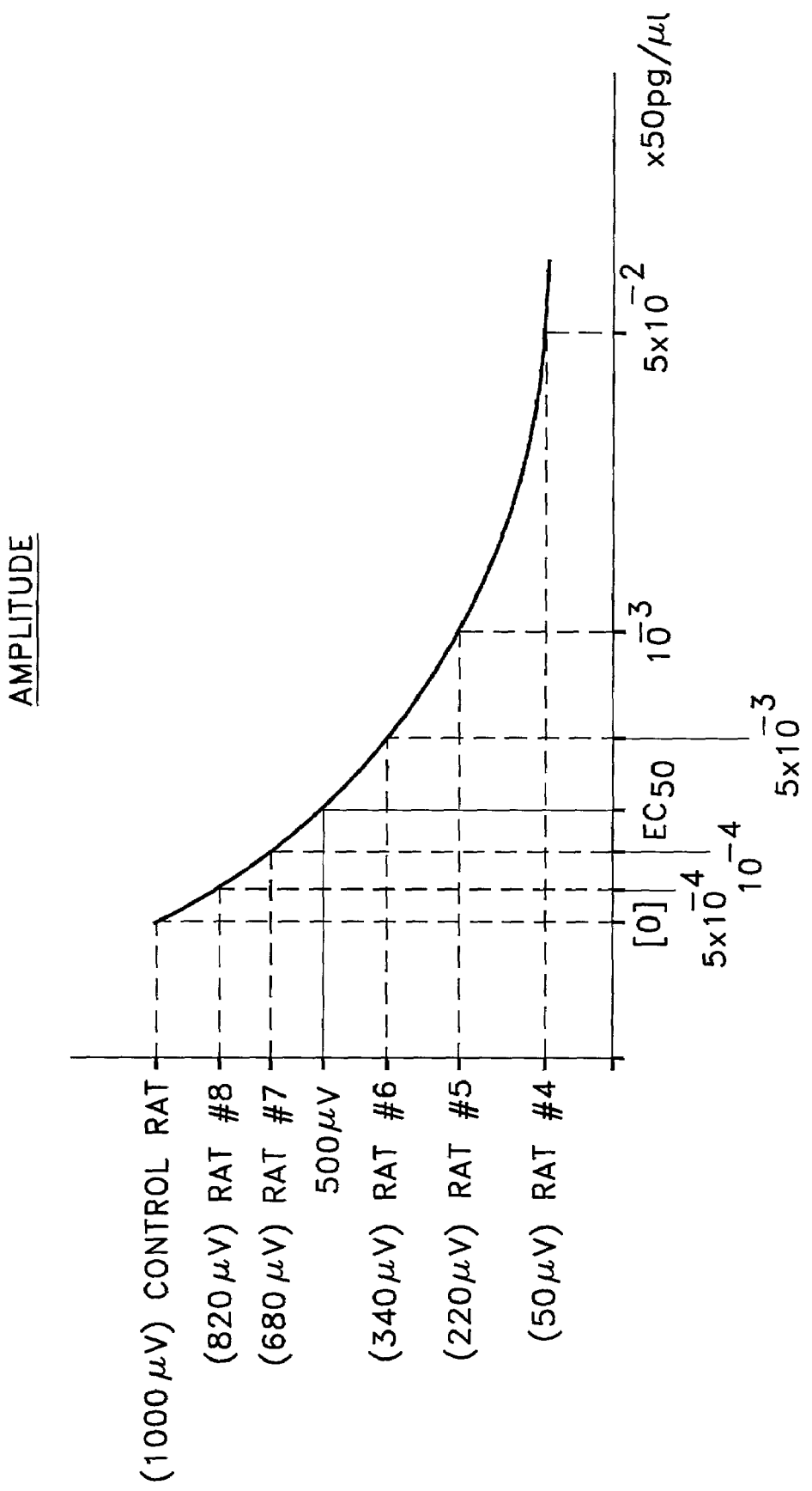
FIG. 3 is a dose response curve showing reduction in amplitude of muscle activity in rats as measured in accordance with the present invention.

An average is taken of the seven measurements for each of the five rats tested. These mean values are plotted on a dose response curve in order to calculate an amplitude $ED_{50}$ value for the stock botulinum toxin type A solution (FIG. 3). It can be seen in FIG. 3 that the amplitude $ED_{50}$ value (potency) for the stock botulinum toxin solution is between $10^{-4} \times (50\ picograms/microliter)$ and $5 \times 10^{-3} \times (50\ picograms/microliter)$ per rat. That is, the amplitude of the EMG measured response of a rat injected with between $10^{-4} \times (50\ picograms/microliter)$ and $5 \times 10^{-3} \times (50\ picograms/microliter)$ of botulinum toxin type A will be 50% that of the Control Rat, where the Control Rat has the largest measured amplitude and Rat No. 4 has the smallest measured amplitude.

EXAMPLE 4

Rats are injected with botulinum toxin type A as in Example 1. Change in EMG latency for the EMG measurement is measured for Rats No. 4, 5, 6, 7, 8 and the Control Rat using the assay apparatus previously described. For each of these rats, the EMG latency is determined using seven independent measurements each taken at a 5 minute interval.

Figure 4:
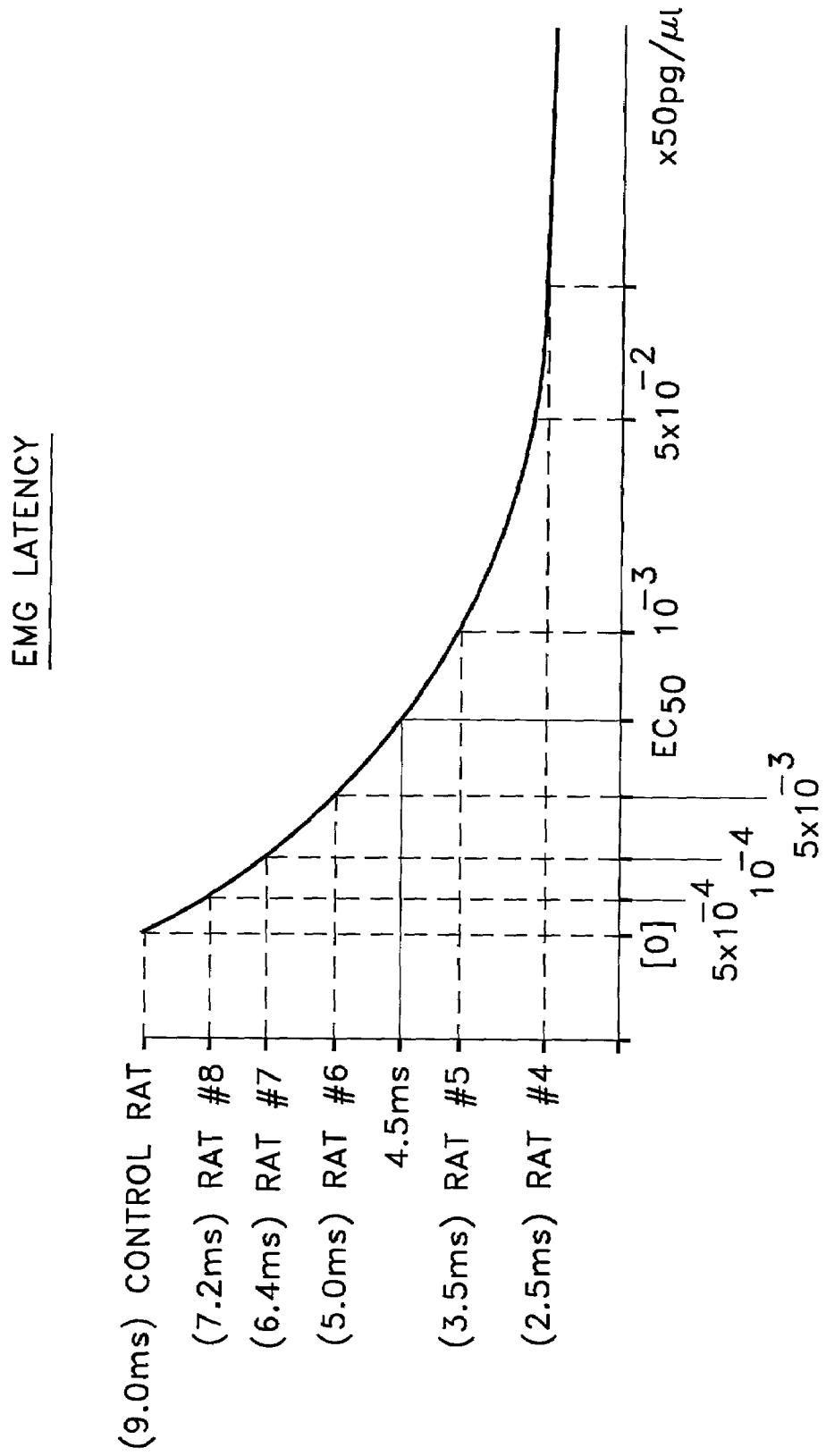
FIG. 4 is a dose response curve showing reduction in EMG latency in rats as measured in accordance with the present invention

An average is taken of the seven measurements for each of the five rats tested. These mean values are plotted on a dose response curve in order to calculate a EMG latency $ED_{50}$ value for the stock botulinum toxin type A solution (FIG. 4). It can be seen in FIG. 4 that the EMG latency $ED_{50}$ value (potency) for the stock botulinum toxin solution is between $5 \times 10^{-3} \times (50\ picograms/microliter)$ and $10^{-3} \times (50\ picograms/microliter)$ per rat. That is, the latency of the EMG measured response of a rat injected with between $5 \times 10^{-3} \times (50\ picograms/microliter)$ and $10^{-3} \times (50\ picograms/microliter)$ of botulinum toxin type-A is half way between the Control Rat and Rat No. 4, where the Control Rat has the shortest measured latency and the Rat No. 4 has the longest measured latency.

EXAMPLE 5

A commercially available preparation of botulinum toxin type A containing 25 nanograms of neurotoxin is purchased from a vendor. The neurotoxin is sterile, vacuum-dried, purified botulinum toxin type A, produced from fermentation of Hall strain *Clostridium botulinum* type A grown in a medium containing casein hydrolysate, glucose and yeast extract. The toxin is purified from the culture medium by dialysis and a series of acid precipitations in a complex consisting of the neurotoxin, and several accessory proteins. The complex is dissolved in sterile sodium chloride solution containing human albumin and is then filtered through a 0.2 micron pore size filter. The solution is then administered to vials and vacuum-dryed.

The freeze dried toxin-protein complex is rehydrated in 5 ml of sterile $dH_2O$. The solution is divided into five 1 ml aliquots. Each aliquot is frozen, packed in dry ice and sent by overnight courier to one of five different analytical laboratories. Each laboratory is set up to perform mouse LD50 assays and rat pinna reflex response assays.

All of the laboratories perform LD50 and pinna reflex response assays using the same protocol. The results are shown below.

|  | Calculated Volume for 1 Mouse LD50 unit | Calculated Volume for 500 magnitude $ED_{50}$ units (see Example 1) |
| --- | --- | --- |
| Lab 1 | 2.0 microliters | 20.1 microliters |
| Lab 2 | 6.1 microliters | 21.1 microliters |
| Lab 3 | 18.9 microliters | 20.5 microliters |
| Lab 4 | 22.3 microliters | 19.8 microliters |
| Lab 5 | 9.4 microliters | 21.3 microliters |

From these data it is clear that the pinna reflex assay is superior to the LD50 assay. Specifically, the range of the mouse LD50 assay in this experiment is greater than 10 fold, high to low, with a percent standard deviation of 59.4%. This is in sharp contrast to the variability of the pinna reflex assay where the range is within 10%, high to low, with a percent standard deviation of 2.5%.

These data show the pinna reflex response assay represents a substantial improvement in the reproducibility of botulinum toxin type A potency analysis over the conventional LD50 assay.

While this invention has been described with respect to various specific examples and embodiments, it is to be understood that the invention is not limited thereto and that it can be variously practiced within the scope of the following claims.

What is claimed is:

1. A method for measuring potency of a Clostridial neurotoxin, said method comprising:
   injecting a Clostridial neurotoxin into a muscle of a mammal;
   subjecting said mammal to a stimulus; and
   monitoring a pinna reflex response of said mammal to said stimulus to measure the potency of the Clostridial neurotoxin; wherein said monitoring includes measuring a latency of the response.

2. The method of claim 1 which further comprises placing said mammal in a confined space prior to said subjecting.

3. The method of claim 1 which further comprises placing said mammal in a restraint prior to said subjecting.

4. The method of claim 2 which further comprises placing said mammal in a restraint in said confined space prior to said subjecting.

5. The method of claim 1 wherein said monitoring includes recording said pinna reflex response of said mammal to said stimulus.

6. The method of claim 1 wherein said mammal is a rat.

7. The method of claim 1 wherein the Clostridial neurotoxin is injected into a levator auris longus muscle of said mammal.

8. The method of claim 1 wherein the Clostridial neurotoxin is a toxin selected from the group consisting of botulinum toxin serotype A, botulinum serotype B, botulinum serotype C1, botulinum toxin serotype D, botulinum toxin serotype E, borulinum toxin serotype F, and combinations thereof.

9. The method of claim 2 wherein the Clostridial neurotoxin is botulinum toxin serotype A.

10. The method of claim 1 wherein said stimulus has an effect on a sense of said mammal.

11. The method of claim 1 wherein said stimulus is an acoustic stimulus or a visual stimulus.

12. The method claim 1 wherein said stimulus is an acoustic stimulus.

13. The method of claim 1 wherein said monitoring includes using a photocell device.

14. The method of claim 1 wherein said monitoring comprises measuring a flexion of an ear of said mammal.

15. The method of claim 14 wherein said measuring includes using a photocell device positioned in front of said ear of said mammal.

16. The method of claim 14 wherein said measuring includes recording said flexion of said ear of said manual.

17. The method of claim 1 which further comprises monitoring an activity of the muscle injected with the Clostridial neurotoxin.

18. The method of claim 17 wherein said muscle activity monitoring includes using an electromyograph.

19. The method of claim 17 wherein said muscle activity monitoring includes recording said activity of said muscle.

20. The method of claim 17 which further comprises repeating said subjecting and said activity monitoring after a time interval has elapsed.

21. The method of claim 17 which further comprises repeating said subjecting and said activity monitoring after a pre-determined time interval has elapsed.

22. The method of claim 17 further comprising correlating said activity to said potency of said Clostridial neurotoxin.

23. The method of claim 1 which further comprises monitoring an activity of the muscle injected with the Clostridial neurotoxin by appropriately positioning an electromyographical probe.

24. The method of claim 23 wherein said muscle activity monitoring includes recording information provided by said electromyographical probe.

25. The method of claim 1 which further comprises repeating said subjecting and said monitoring after a time interval has elapsed.

26. The method of claim 23 wherein said information is an amplitude of said response.

27. The method of claim 23 wherein said information is a frequency of said response.

28. The method of claim 23 wherein said information is a substance latency of said response.

29. The method of claim 1 which further comprises repeating said subjecting and said monitoring after a pre-determined time interval has elapsed.

30. The method of claim 1 which includes measuring a magnitude of said response.

31. The method of claim 1 further comprising correlating said response to said potency of said Clostridial neurotoxin.

32. The method of claim 31 wherein said correlating is done using a member selected from the group consisting of a latency, an EMG latency, a magnitude, an amplitude, a frequency and combinations thereof.

33. The method of claim 1 wherein more than one dose level of said Clostridial neurotoxin is administered to said mammal.

34. A method for measuring potency of a Clostridial neurotoxin, said method comprising:
   injecting a Clostridial neurotoxin into a muscle of each of a plurality of mammals, each mammal being provided with a different dose level of Clostridial neurotoxin;
   subjecting said mammals to a stimulus and;
   monitoring a pinna reflex response of said mammals to said stimulus to measure the potency of the Clostridial neurotoxin; wherein said monitoring includes measuring a latency of the response.

35. The method of claim 34 wherein said monitoring includes recording said pinna reflex response of said mammal to said stimulus.

36. The method of claim 34 wherein said mammal is a rat.

37. The method of claim 34 wherein the Clostridial neurotoxin is botulinum toxin serotype A.

38. The method claim 34 wherein said stimulus is an acoustic stimulus.

39. The method of claim 34 which further comprises monitoring an activity of the muscle injected with the Clostridial neurotoxin.

40. The method of claim 34 which further comprises repeating said subjecting and said monitoring after a time interval has elapsed.

41. The method of claim 34 which includes measuring a response magnitude.

* * * * *